United States Patent [19]
Petterson

[11] Patent Number: 6,010,002
[45] Date of Patent: Jan. 4, 2000

[54] PACKAGE FOR HOUSING A SELF-ADHESIVE BANDAGE

[76] Inventor: Tor Petterson, 31248 Palos Verdes Dr. West, Rancho Palos Verdes, Calif. 90274

[21] Appl. No.: 09/136,485

[22] Filed: Aug. 19, 1998

[51] Int. Cl.$^7$ .................................................. A61F 13/00
[52] U.S. Cl. ............................................ 206/441; 206/440
[58] Field of Search ................................. 206/440, 441; 602/54, 57

[56] References Cited

U.S. PATENT DOCUMENTS

| | | |
|---|---|---|
| 4,265,234 | 5/1981 | Schaar . |
| 4,917,929 | 4/1990 | Heinecke . |
| 5,780,048 | 7/1998 | Lee . |

*Primary Examiner*—David T. Fidei
*Attorney, Agent, or Firm*—Sheldon & Mak; Denton L. Anderson

[57] ABSTRACT

A combination of a planar substrate and a package for housing the planar substrate, such as a self-adhesive bandage, is provided. In the invention, the package is made up of two opposed package portions. One wall of each package portion is elongated so that it can be folded inwardly on itself to provide protection for the opposed adhesive-coated ends of the substrate. By this design, the package can be simply opened by pulling the two package portions apart. The opening of the package also automatically exposes the adhesive-covered ends of the substrate. The user can therefore apply the substrate without ever having to take his or her hands off of the opposed ends of the package. The invention thereby provides a unique package for housing self-adhesive bandages which greatly simplifies the package opening process and which substantially eliminates the danger of contacting the sterile pad portion of the bandage or getting entangled with the adhesive portions of the bandage.

21 Claims, 5 Drawing Sheets

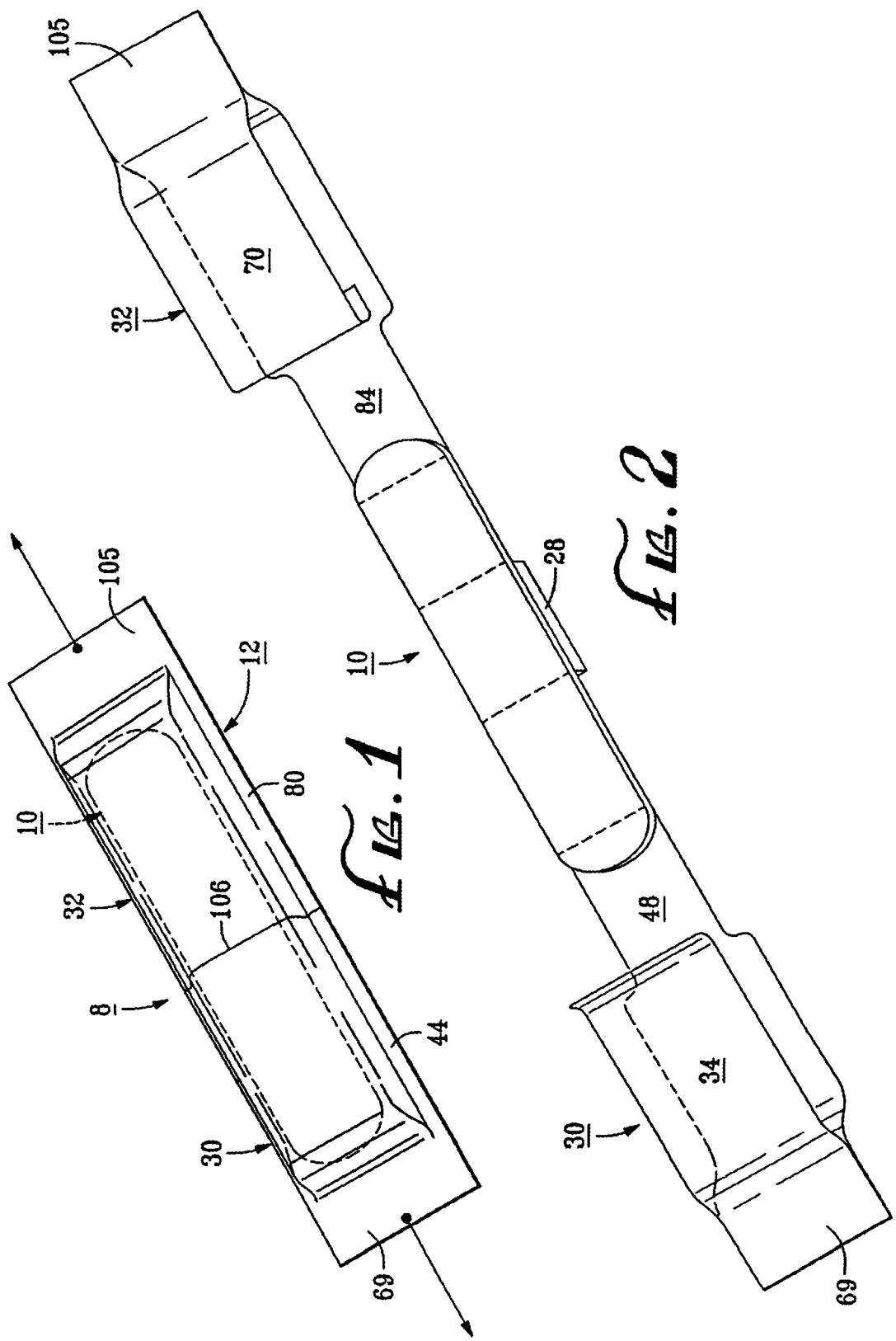

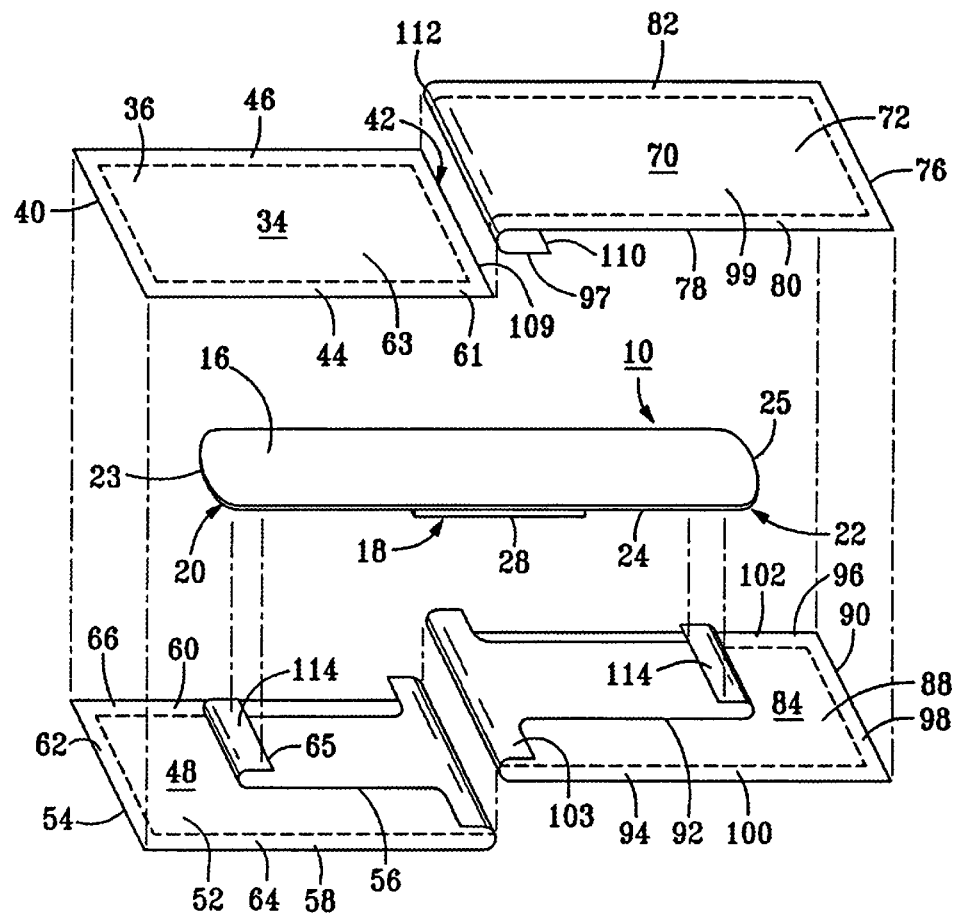
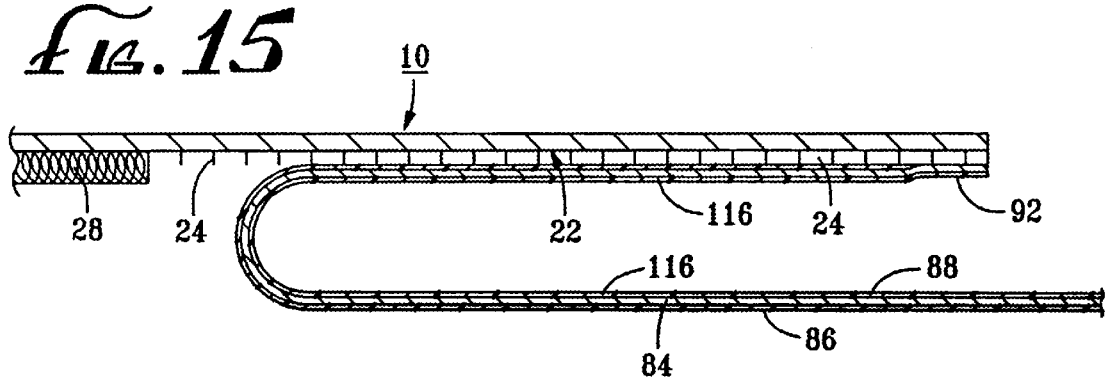

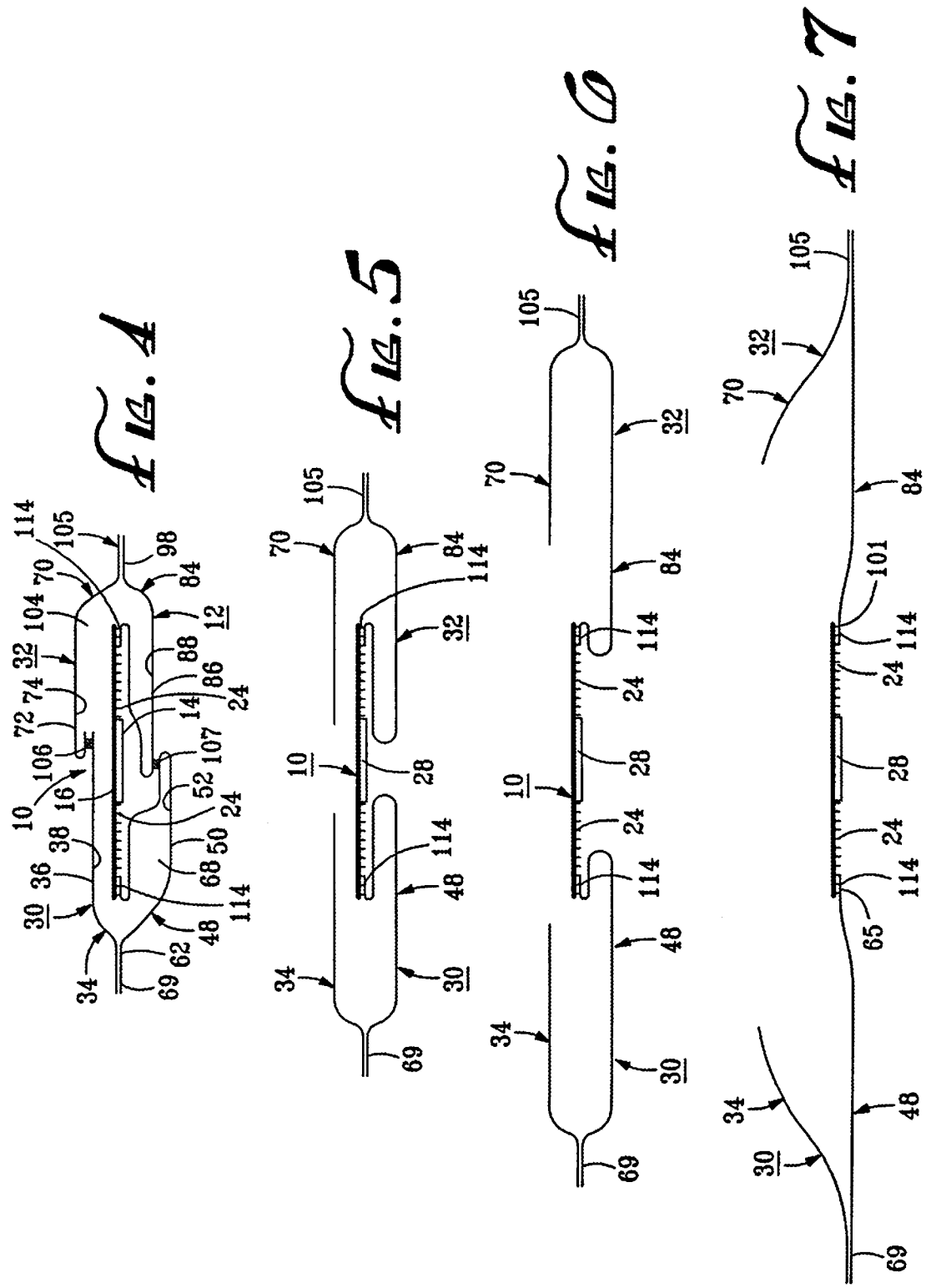

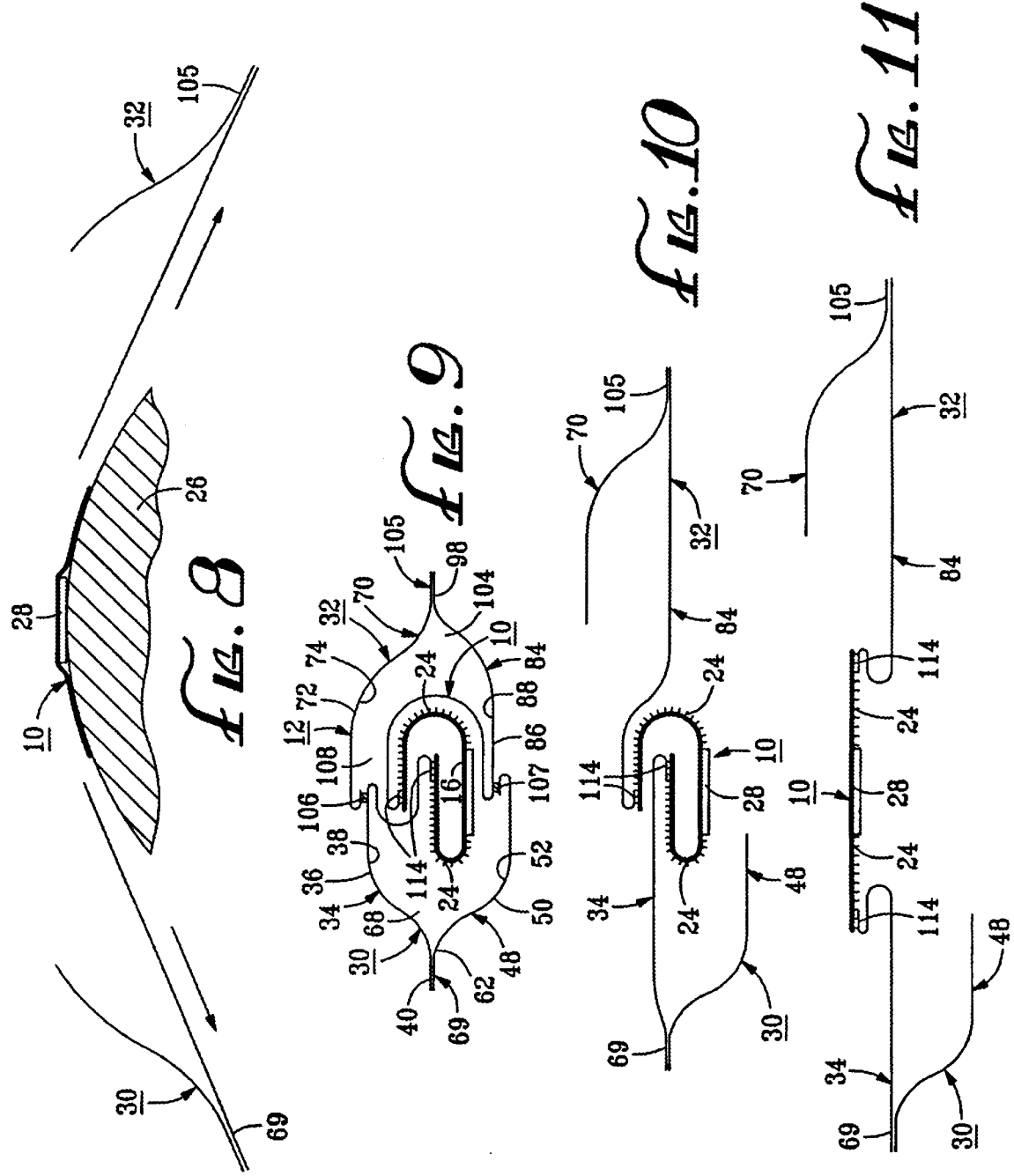

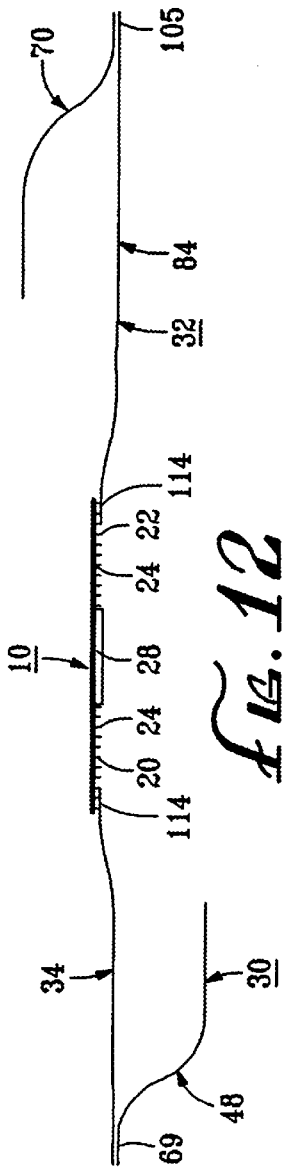
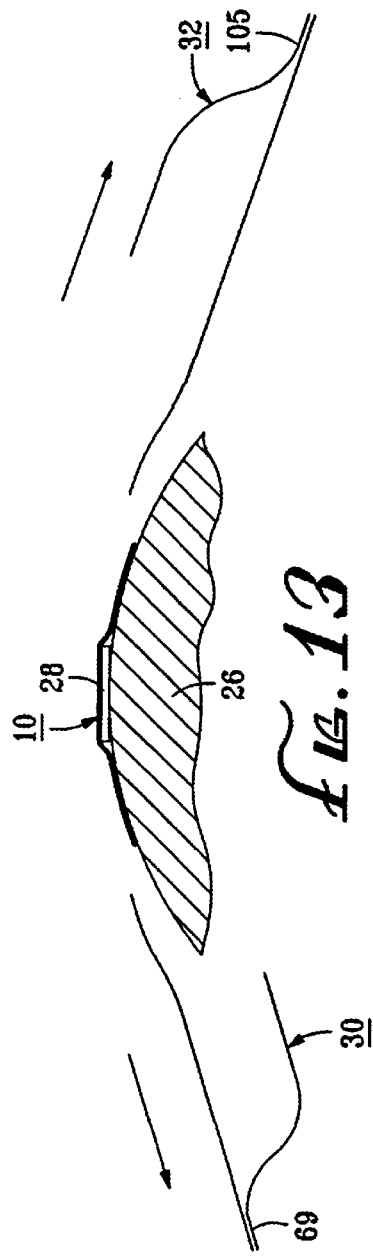
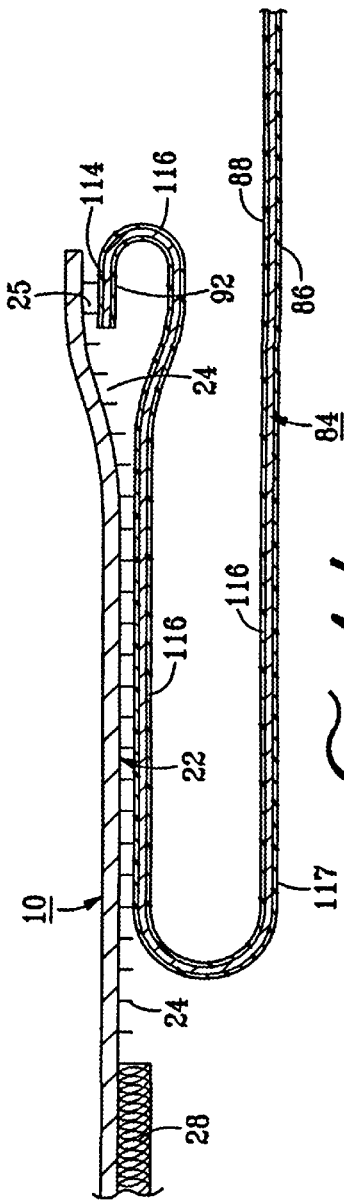

PACKAGE FOR HOUSING A SELF-ADHESIVE BANDAGE

FIELD OF THE INVENTION

This invention relates generally to packages for planar substrates, and, more particularly, to packages for housing self-adhesive planar substrates, such as a self-adhesive bandages.

BACKGROUND OF THE INVENTION

A variety of planar substrates must be individually packaged to preserve cleanliness of the substrate. The most common such planar substrate is a self-adhesive bandage having opposed, adhesive-coated end portions and a sterile central pad portion. To preserve the sterility of the pad portion, such self-adhesive bandages are normally packaged in individual sealed "envelopes."

Although such envelopes satisfactorily maintain the sterility of the bandage, there are several problems with the use of such envelopes. Firstly, the envelopes are frequently difficult to open. The most commonly used envelope, for example, requires tearing open the envelope using an internally attached piece of thread. Manipulating this piece of thread can be frustratingly difficult, especially if wearing protective gloves. Moreover, occasionally the internal attachment of the thread breaks—wholly disabling the opening mechanism.

Secondly, once the envelope is opened, an additional problem is raised as to how to administer the bandage without soiling the sterile pad and without becoming entangled with the adhesive-coated ends. In almost all self-adhesive bandages on the market, the opposed adhesive-covered ends are protected with separate cover sheets. It can be exceedingly difficult to remove these cover sheets without contacting either the adhesive-covered ends or the sterile pad. The difficulty inherent in removing the protective sheets is magnified when the caregiver is wearing protective gloves. Typically, such gloves are made from a very thin material to which the adhesive on the bandage readily attaches. Accordingly, it can seem almost impossible to manipulate a simple self-adhesive bandage from package to patient by a caregiver wearing protective gloves.

Accordingly, there is a need for a package which eliminates the above-described problems with the prior art.

SUMMARY

The invention satisfies this need. The invention is a combination of a planar substrate, such a self-adhesive bandage, and a package for housing that substrate. The substrate has a front side and a back side. On the front side of the substrate, there is a central portion (where can be disposed a sterile pad) and opposed first and second end portions, at least one having an adhesive coating disposed thereon.

The package comprises a first package moiety and a second package moiety. The first package moiety comprises (i) a rearward sheet having an exterior side and an interior side, having opposed distal and proximal ends and having opposed first and second side edges and (ii) a forward sheet having an exterior side and an interior side, having opposed distal and proximal ends and having opposed first and second side edges, wherein the distal ends of the rearward and forward sheets of the first package moiety are sealed together, wherein the first side edges of the rearward and forward sheets of the first package moiety are sealed together and wherein the second side edges of the rearward and forward sheets of the first package moiety are sealed together, in each case with the interior sides of the rearward and forward sheets of the first package moiety facing one another, so that the first package moiety forms a first partial enclosure.

The second package moiety comprises (i) a first rearward sheet having an exterior side and an interior side, having opposed distal and proximal ends and having opposed first and second side edges, and (ii) a forward sheet having an exterior side and an interior side, having opposed distal and proximal ends and having opposed first and second side edges, wherein the distal ends of the rearward and forward sheets of the second package moiety are sealed together, wherein the first side edges of the rearward and forward sheets of the second package moiety are sealed together and wherein the second side edges of the rearward and forward sheets of the second package moiety are sealed together, in each case with the interior sides of the rearward and forward sheets of the second package moiety facing one another, so that the second package moiety forms a second partial enclosure.

The proximal end of each sheet includes a tip portion and an inward portion. The proximal end of at least one of the sheets in the first package moiety is folded and disposed with its exterior side in contact with an adhesive layer on the front side of the substrate. Similarly, the proximal end of at least one of the sheets in the second package moiety is folded and disposed with its exterior side in contact with an adhesive layer on the front side of the substrate.

The two proximal ends of the rearward sheets of the first and second package moieties are sealed together and the two proximal ends of the forward sheets of the first and second package moieties are sealed together, so that the first and second package moieties cooperate to provide a sealed enclosure with the substrate disposed therein.

The invention provides the caregiver with the unique ability to open the package, remove the sheets which protect the adhesive surfaces and apply the bandage to a patient in a one-step operation by merely grasping the package at opposite ends and gently pulling the first and second package moieties apart. This simple pulling apart of the package not only opens the package, but also automatically removes the protective sheets from the adhesive portions of the bandage. Finally, while continuing to grasp the opposite ends of the two package moieties, the bandage can be administered to a patient. There is no need to deal with a myriad of individual parts of the bandage package, and there is no risk of the caregiver contacting either with the sterile pad portion of the adhesive portions.

DRAWINGS

These features, aspects and advantages of the present invention will become better understood with regard to the following description, appended claims and accompanying figures where:

FIG. 1 is a perspective view of a combination having features of the invention;

FIG. 2 is a perspective view of the combination illustrated in FIG. 1, shown in partial disassembly, as during application;

FIG. 3 is an exploded perspective view of the combination as shown in FIG. 1 having features of the invention;

FIG. 4 is a schematic side view of the combination illustrated in FIG. 1;

FIG. 5 is a schematic side view of the combination illustrated in FIG. 1 showing the two combination moieties drawn partially apart;

FIG. 6 is a schematic side view of the combination illustrated in FIG. 1 showing the two combination moieties drawn further apart than shown in FIG. 5;

FIG. 7 is a schematic side view of the combination illustrated in FIG. 1 showing the two combination moieties drawn further apart than shown in FIG. 6;

FIG. 8 is a schematic side view of a self-adhesive bandage applied to a patient using the combination illustrated in FIG. 1;

FIG. 9 is a schematic side view of a second combination having features of the invention;

FIG. 10 is a schematic side view of the combination illustrated in FIG. 9 showing the two combination moieties drawn partially apart;

FIG. 11 is a schematic side view of the combination illustrated in FIG. 9 showing the two combination moieties drawn further apart than shown in FIG. 10;

FIG. 12 is a schematic side view of the combination illustrated in FIG. 9 showing the two combination moieties drawn further apart than shown in FIG. 11;

FIG. 13 is a schematic side view of a self-adhesive bandage applied to a patient using the combination illustrated in FIG. 9;

FIG. 14 is a schematic side view detail of a self-adhesive bandage and package having features of the invention; and FIG. 15 is a side view detail of an alternative self-adhesive bandage having features of the invention.

DETAILED DESCRIPTION

The following discussion describes in detail one embodiment of the invention and several variations of that embodiment. This discussion should not be construed, however, as limiting the invention to those particular embodiments. Practitioners skilled in the art will recognize numerous other embodiments as well.

The invention is a combination 8 of a planar substrate 10 disposed within a unique package 12. As illustrated in the drawings and as hereinafter described, the planar substrate 10 is most typically a self-adhesive bandage. However, it will be appreciated by those skilled in the art that the planar substrate 10 can be other than a self-adhesive bandage. In all cases, the planar substrate 10 has a front side 14 and a back side 16. The front side 14 comprises a central portion 18 and opposed first and second end portions 20 and 22, respectively. Both the first and second end portions 20 and 22 each have a distal-most end 23 and 25, respectively. Disposed on the front side 14 of the substrate 12, and typically on each end portion 20 and 22, is an adhesive layer 24 suitable for adhering the planar substrate 10 to a target surface 26. Where the planar substrate 10 is a self-adhesive bandage, the central portion 18 includes a sterile pad 28 and the target surface 26 is the skin of a patient.

The package 12 comprises a first package moiety 30 and a second package moiety 32. The first package 30 moiety includes a rearward sheet 34 having an exterior side 36 and an interior side 38, having opposed distal and proximal ends 40 and 42, respectively, and having opposed first and second side edges 44 and 46, respectively. The first package moiety 30 further includes a forward sheet 48 having an exterior side 50 and an interior side 52, having opposed distal and proximal ends 54 and 56, respectively, and having opposed first and second side edges 58 and 60, respectively. The proximal end 42 of the rearward sheet 34 of the first package moiety 30 has a tip portion 61 and an inward portion 63. Similarly, the proximal end 56 of the forward sheet 48 of the first package moiety 30 has a tip portion 65 and an inward portion 67. The distal ends 40 and 54 of the rearward and forward sheets of the first package moiety 30 are joined together at a first distal end joint 62 to provide a first package moiety distal end 69. The first side edges 44 and 58 of the rearward and forward sheets 34 and 48 of the first package moiety 30 are joined together at a first side edge joint 64, and the second side edges 46 and 60 of the rearward and forward sheets 34 and 48 of the first package moiety 30 are joined together at a second side edge joint 66. Each such joint 62, 64 and 66 can be accomplished, for example, by folding the sheets, by use of a permanent sealing adhesive or by use of a suitable heat sealing process. Each joint 62, 64 and 66 is made such that the interior sides 38 and 52 of the rearward and forward sheets 34 and 48 of the first package moiety face each other. After the joining of the distal ends 40 and 54 and the side edges 44 and 58, 46 and 60, the first package moiety 30 forms a first partial enclosure 68.

The second package moiety 32 includes a rearward sheet 70 having an exterior side 72 and an interior side 74, having opposed distal and proximal ends 76 and 78, respectively, and having opposed first and second side edges 80 and 82, respectively. The second package moiety 32 further includes a forward sheet 84 having an exterior side 86 and an interior side 88, having opposed distal and proximal ends 90 and 92, respectively, and having opposed first and second side edges 94 and 96, respectively. The proximal end 78 of the rearward sheet of the second package moiety 32 has a tip portion 97 and an inward portion 99. Similarly, the proximal end 92 of the forward sheet 84 of the second package moiety 32 has a tip portion 101 and an inward portion 103. The distal ends 76 and 90 of the rearward and forward sheets 70 and 84 of the second package moiety 32 are joined together at a second distal end joint 98 to provide a second package moiety distal end 105. The first side edges 80 and 94 of the rearward and forward sheets 70 and 84 of the second package moiety 32 are joined together at a third side edge joint 100, and the second side edges 82 and 96 of the rearward and forward sheets 70 and 84 of the second package moiety 32 are joined at a fourth side edge joint 102. Each such joint 98, 100 and 102 can be accomplished, for example, by folding the sheets, by use of a permanent sealing adhesive or by use of a suitable heat sealing process. Each joint 98, 100 and 102 is made such that the interior sides 74 and 88 of the rearward and forward sheets 70 and 84 of the second package moiety 32 face each other. After the joining of the distal ends 76 and 90 and the side edges 80 and 94, 82 and 96, the second package moiety 32 forms a second partial enclosure 104.

Typically, each of the sheets 34, 48, 70 and 84 in the first and second package moieties 30 and 32 are made from a non-woven material, such as a paper or flexible plastic material.

The proximal end 42 and/or 56 of at least one of the sheets 34 and 48 of the first package moiety 30 is folded and disposed with its exterior side 36 and/or 50 in contact with the adhesive layer 24 on the front side 14 of the substrate 10. Similarly, the proximal end 78 and/or 92 of at least one of the sheets 70 and 84 of the second package moiety 32 is folded and disposed with its exterior side 72 and/or 86 in contact with an adhesive layer 24 on the front side 14 of the substrate 10.

FIGS. 1–8 illustrate one embodiment of the invention. In this embodiment, the proximal end 56 of the forward sheet 48 of the first package moiety 30 is folded and disposed with its exterior side 50 in contact with the adhesive layer 24 on the front side 14 of the first end portion 20 of the substrate 10. Also in this embodiment, the proximal end 92 of the forward sheet 84 of the second package moiety 32 is folded and disposed with its exterior side 86 in contact with the adhesive layer 24 on the front side 14 of the second end portion 22 of the substrate 10.

FIGS. 9–13 illustrate a second embodiment of the invention. In this embodiment, the proximal end 42 of the rearward sheet 34 of the first package moiety 30 is folded and disposed with its interior side 38 in contact with the adhesive layer 24 on the front side 14 of the first end portion 20 of the substrate 10. Also in this embodiment, the proximal end 92 of the forward sheet 84 of the second package moiety 32 is folded and disposed with its exterior side 86 in contact with the adhesive layer 24 on the front side 14 of the second end portion 22 of the substrate 10.

In all embodiments, the two proximal ends 42 and 78 of the rearward sheets 34 and 70 of the first and second package moieties 30 and 32 are joined together at a rearward proximal end joint 106, and the two proximal ends 56 and 92 of the forward sheets 48 and 84 of the first and second package moieties 30 and 32 are joined together at a forward proximal end joint 107. Thus, the first and second package moieties 30 and 32 cooperate to provide an enclosure 108 with the substrate 10 disposed therein. In the embodiment illustrated in FIGS. 1–8, the two proximal ends 42 and 78 of the rearward sheets 34 and 70 of the first and second moieties 30 and 32 are joined together near their proximal-most ends 109 and 110, respectively. Preferably, the proximal-most ends 109 and 110 of one of the rearward sheets 34 or 70 is folded at a fold 112 so that the interior surfaces 38 and 74 of the two proximal-most ends 109 and 110 are joined together. Also in the embodiment illustrated in FIGS. 1–8, the inward portions 67 and 103 of the proximal ends 56 and 92 of the forward sheets 48 and 84 are joined together. Each proximal end 56 and 92 of the forward sheets 48 and 84 is folded so that the exterior sides 50 and 86 of both proximal ends 56 and 92 of the forward sheets 48 and 84 can be disposed in contact with the adhesive layer 24 on the front side 14 of the substrate 10. In this embodiment, the proximal ends 56 and 92 of the forward sheets 48 and 84 are joined together at their respective inward portions 67 and 103, such that the external sides 50 and 86 of the two inward portions 67 and 103 of the proximal ends 56 and 92 of the forward sheets 48 and 84 are joined together.

In the embodiment illustrated in FIGS. 9–13, one of the proximal ends 42 or 78 of the rearward sheets 34 or 70 is folded so that the proximal end 42 or 78 of that sheet 34 or 70 can be disposed in contact with the adhesive layer 24 on the front side 14 of the substrate 10. The joining of both the rearward sheets 34 and 70 and the forward sheets 36 and 72 is accomplished by joining the tip portion 61 or 97 of one of the proximal ends 42 or 78 to the inward portion 63 or 99 of the other proximal end 42 or 78. Preferably, the forward proximal end joint 107 is made such that the exterior sides 36 and 72 of both sheets 34 and 70 are joined together.

In all embodiments, it is also preferable that the proximal ends 42 and 78 of the rearward sheets 34 and 70 of the first and second package moieties 30 and 32 and the proximal ends 56 and 92 of the forward sheets 48 and 84 of the first and second package moieties 30 and 32 are both joined together by folding, by use of a low tack adhesive or by some similar reversible joining mechanism. This allows the joints 106 and 107 between the proximal ends 42 and 78 of the rearward sheets 34 and 70 and the forward sheets 48 and 84 to be easily and gradually broken by gently pulling on opposite distal ends 69 and 105 of the first and second package moieties 30 and 32.

In a still further preferred embodiment, one of the tip portions 61 or 65 of the proximal ends 42 and 56 of the sheets 34 or 48 of the first package moiety 30 is folded so that a tab 114 is formed at the end of each tip portion 61 or 65. Likewise, in this still preferred embodiment, one of the tip portions 97 or 101 of the proximal ends 78 and 92 of the sheets 70 and 84 of the second package moiety 32 is folded so that a tab 114 is formed at the end of each tip portion 97 or 101. Each tab 114 is between about 1 mm and about 10 mm long. Each tab 14 is disposed in contact with the adhesive layer 24 on the front side 14 of the substrate 10 at opposite end portions of the substrate 10. This feature is illustrated in each of the drawings, but is most easily seen in FIG. 14.

In the embodiment illustrated in FIG. 14, the entire interior side 88 of the forward sheet 84 is coated with a high adherence material 116, such as polyethylene. Conversely, the entire exterior side 86 of the forward sheet 84 is coated with a low adherence layer 117, such as a non-stick fluorocarbon, such as Teflon® brand materials manufactured and sold by the DuPont Chemical Company of Wilmington, Del. The high adherence layer 116 has little propensity to adhere to itself, but does strongly adhere to the adhesive layer 24 on the front side 14 of the substrate 10. The low adherence layer 117, on the other hand, adheres to a much lesser extent to the adhesive layer 24. In the preferred embodiment illustrated in FIG. 14, the only material in contact with the adhesive layer 24 is the low adherence layer 117, except for the high adherence layer 116 on the tab 114. By this design, the forward sheet 84 can be readily peeled away from the adhesive layer 24 until the only contact between the adhesive layer 24 and the forward sheet 84 is the tab 114. Pulling the tab 114 away from the adhesive layer 24 requires a modestly sharp tug on the distal end 90 of the forward sheet 84.

In embodiments wherein the high adherence layer 116 is polyethylene, the side edges 44, 46, 58 and 60 and the distal ends 69 and 105 of the first and second package moieties 30 and 32 can be heat-sealed by heating the polyethylene at the respective side edges and distal ends, whereupon the opposed polyethylene layers 116 rigidly adhere to one another. In a typical embodiment, the width of the substrate 10 is about 0.75 inches and the package 12 has a width of about 1.25 inches. Accordingly, approximately 0.125 inches along each side edge 44, 46, 58 and 60 can be heat-sealed in the manner described above.

This tab feature provides additional assurance that the distal-most ends 23 and 25 of the adhesive-covered end portions 20 and 22 of the substrate 10 will remain in firm contact with the tip portion of a sheet within each package moiety 30 and 32 during application of the substrate 10 to the target surface 26 (as illustrated in FIGS. 7 and 12). The tabs 114 can only be pulled away from the distal-most ends 23 and 25 of the substrate 10 in a synchronized "high force" release which frees both tabs 114 simultaneously. Without this feature, the distal-most ends 23 and 25 of one or both of the adhesive-covered ends 20 and 22 of the substrate 10 might prematurely disengage from its respective package moiety 30 or 32 during application of the substrate 10.

FIG. 15 illustrates an alternative embodiment (alternative to the preferred embodiment illustrated in FIG. 14). In the embodiment illustrated in FIG. 15, instead of the tip portions 61 or 65 and 97 or 101 being folded over to provide tabs 114, the tip portions 61 or 65 and 97 or 101 are disposed flat against the adhesive layer 24. To provide a synchronized "high force" release similar to that provided by the embodiment illustrated in FIG. 14, the tip portions 61 or 65 and 97 or 101 in the embodiment illustrated in FIG. 15 are provided with a high adherence surface relative to the non-tip surface disposed against the adhesive layer 24. Such high adherence surface can be provided by selectively coating the tip portions 61 or 65 and 97 or 101 with a high adherence layer 116, such as polyethylene. Alternatively, the high adherence surface can be provided as illustrated in FIG. 15 by merely leaving the tip portions 61 or 65 and 97 or 101 wholly uncoated and coating the non-tip portions with a low adherence layer 117.

In operation, the package 12 of the invention can be conveniently opened and the substrate 10 applied to the target surface 26 in one continuous operation—by merely gripping the opposed distal ends 69 and 105 of the package 12 and gently pulling those two distal ends 69 and 105 apart. In the embodiment illustrated in FIGS. 1–8, this operation is easily seen by reference to FIGS. 4–8. In the embodiment illustrated in FIGS. 9–13, this operation is easily seen by reference to FIGS. 9–13. FIGS. 4 and 9 represent the two different embodiments of the package 12 before opening is commenced. In FIGS. 5 and 10, the user grips the opposed distal ends 69 and 105 of the package 12 and begins to gently pull outwardly on those two distal ends 69 and 105. The easily broken joints 106 and 107 are gradually broken. The user then continues to gradually pull the opposed distal ends 69 and 105 further apart as illustrated in FIGS. 6 and 11. As the user does so, the proximal ends of each sheets from the two package moieties 30 and 32 which are in contact with the adhesive layer 24 on the substrate 10 are gradually pulled away from the adhesive layer 24. The user ceases to pull on the distal ends 69 and 105 of the package 12 when the only contact between the package moieties 30 and 32 and the substrate 10 is provided by contact with a tab 114 from one of the sheets of each package moiety 30 and 32 (as illustrated in FIGS. 7 and 12). The user then, while holding the opposed distal ends 69 and 105 with the substrate 10 and package moieties 30 and 32 construed as shown in FIGS. 7 and 12, applies the substrate 10 to the target surface 26. Thereafter, the user pulls slightly further on the opposed distal ends 69 and 105 of the package 12 until both package moieties 30 and 32 are fully disengaged from the substrate 10 (as illustrated in FIGS. 8 and 13).

Having thus described the invention, it should be apparent that numerous structural modifications and adaptations may be resorted to without departing from the scope and fair meaning of the instant invention as set forth hereinabove and as described hereinbelow by the claims.

What is claimed is:

1. A combination of a planar substrate and a package for housing the planar substrate, the substrate having a front side and a back side, the front side comprising a central portion and opposed first and second end portions, at least one end portion having an adhesive coating disposed thereon, the package comprising:

(a) a first package moiety comprising (i) a rearward sheet having an exterior side and an interior side, having opposed distal and proximal ends and having opposed first and second side edges and (ii) a forward sheet having an exterior side and an interior side, having opposed distal and proximal ends and having opposed first and second side edges, wherein the distal ends of the rearward and forward sheets of the first package moiety are joined together, wherein the first side edges of the rearward and forward sheets of the first package moiety are joined together and wherein the second side edges of the rearward and forward sheets of the first package moiety are joined together, in each case with the interior sides of the rearward and forward sheets of the first package moiety facing one another, so that the first package moiety forms a first partial enclosure; and (b) a second package moiety comprising (i) a first rearward sheet having an exterior side and an interior side, having opposed distal and proximal ends and having opposed first and second side edges, and (ii) a forward sheet having an exterior side and an interior side, having opposed distal and proximal ends and having opposed first and second side edges, wherein the distal ends of the rearward and forward sheets of the second package moiety are joined together, wherein the first side edges of the rearward and forward sheets of the second package moiety are joined together and wherein the second side edges of the rearward and forward sheets of the second package moiety are joined together, in each case with the interior sides of the rearward and forward sheets of the second package moiety facing one another, so that the second package moiety forms a second partial enclosure;

wherein the proximal end of at least one of the sheets of the first package moiety is folded and disposed with its exterior side in contact with an adhesive layer on the front side of the substrate;

wherein the proximal end of at least one of the sheets of the second package moiety is folded and disposed with its exterior side in contact with an adhesive layer on the front side of the substrate;

wherein the proximal ends of each sheet include a tip portion and an inward portion;

wherein the tip portions of the proximal ends of at least one of the sheets of each of the first and second package moieties are folded together so that a tab is formed at the end of each folded together tip portion with each tab being between about 1 mm and about 10 mm long and wherein each tab is disposed in contact with the adhesive layer on the front side of the substrate at opposite end portions of the substrate;

wherein the two proximal ends of the rearward sheets of the first and second package moieties are joined together; and wherein the two proximal ends of the forward sheets of the first and second package moieties are joined together;

so that, the first and second package moieties cooperate to provide a joined enclosure with the substrate disposed therein.

2. The combination of claim 1 wherein a pad is disposed on the central portion of the front side of the substrate.

3. The combination of claim 2 wherein the pad is sterile.

4. The combination of claim 1 wherein the planar substrate is a self-adhesive bandage.

5. The combination of claim 1 wherein the proximal end of the forward sheet of the first package moiety is folded and disposed with its exterior side in contact with an adhesive layer on the front side of the substrate.

6. The combination of claim 1 wherein the proximal end of the rearward sheet of the first package moiety is folded and disposed with its interior side in contact with an adhesive layer on the front side of the substrate.

7. The combination of claim 1 wherein the sheets are made from a paper.

8. The combination of claim 1 wherein the sheets are made from a flexible plastic.

9. The combination of claim 1 wherein the distal ends of the rearward sheets of the first and second package moieties are joined together with a low tack adhesive.

10. The combination of claim 1 wherein the distal ends of the forward sheets of the first and second package moieties are joined together with a low tack adhesive.

11. The combination of claim 1 wherein each tab is adhered to the adhesive layer using a high adherence material.

12. The combination of claim 1 wherein the interior sides of the forward sheets are coated with a high adherence material.

13. The combination of claim 12 wherein the high adherence material is polyethylene.

14. The combination of claim 1 wherein the exterior side of the forward sheet is coated with a low adherence material.

15. The combination of claim 14 wherein the low adherence material is a fluorocarbon.

16. The combination of claim 1 wherein the tip portions of the proximal ends of at least one of the sheets of each of the first and second package moieties adhere to a greater extent to the adhesive layer than do the non-tip portions of such sheets.

17. The combination of claim 16 wherein the tip portions of the proximal ends of at least one of the sheets of each of the first and second package moieties are uncoated, and the non-tip portions of such sheets are coated with a low adherence material.

18. A combination of a planar substrate and a package for housing the planar substrate, the substrate having a front side and a back side, the front side comprising a central portion and opposed first and second end portions, at least one end portion having an adhesive coating disposed thereon, the package comprising:

(a) a first package moiety comprising (i) a rearward sheet having an exterior side and an interior side, having opposed distal and proximal ends and having opposed first and second side edges and (ii) a forward sheet having an exterior side and an interior side, having opposed distal and proximal ends and having opposed first and second side edges, wherein the distal ends of the rearward and forward sheets of the first package moiety are joined together, wherein the first side edges of the rearward and forward sheets of the first package moiety are joined together and wherein the second side edges of the rearward and forward sheets of the first package moiety are joined together, in each case with the interior sides of the rearward and forward sheets of the first package moiety facing one another, so that the first package moiety forms a first partial enclosure; and (b) a second package moiety comprising (i) a first rearward sheet having an exterior side and an interior side, having opposed distal and proximal ends and having opposed first and second side edges, and (ii) a forward sheet having an exterior side and an interior side, having opposed distal and proximal ends and having opposed first and second side edges, wherein the distal ends of the rearward and forward sheets of the second package moiety are joined together, wherein the first side edges of the rearward and forward sheets of the second package moiety are joined together and wherein the second side edges of the rearward and forward sheets of the second package moiety are joined together, in each case with the interior sides of the rearward and forward sheets of the second package moiety facing one another, so that the second package moiety forms a second partial enclosure;

wherein the proximal ends of each sheet include a tip portion and an inward portion;

wherein the proximal end of at least one of the sheets of the first package moiety is folded and disposed with its exterior side in contact with an adhesive layer on the front side of the substrate;

wherein the proximal end of at least one of the sheets of the second package moiety is folded and disposed with its exterior side in contact with an adhesive layer on the front side of the substrate;

wherein the proximal end of the rearward sheet of the first package moiety is folded and disposed with its interior side in contact with an adhesive layer on the front side of the substrate;

wherein the two proximal ends of the rearward sheets of the first and second package moieties are joined together; and wherein the two proximal ends of the forward sheets of the first and second package moieties are joined together;

so that, the first and second package moieties cooperate to provide a joined enclosure with the substrate disposed therein.

19. A combination of a planar substrate and a package for housing the planar substrate, the substrate having a front side and a back side, the front side comprising a central portion and opposed first and second end portions, at least one end portion having an adhesive coating disposed thereon, the package comprising:

(a) a first package moiety comprising (i) a rearward sheet having an exterior side and an interior side, having opposed distal and proximal ends and having opposed first and second side edges and (ii) a forward sheet having an exterior side and an interior side, having opposed distal and proximal ends and having opposed first and second side edges, wherein the distal ends of the rearward and forward sheets of the first package moiety are joined together, wherein the first side edges of the rearward and forward sheets of the first package moiety are joined together and wherein the second side edges of the rearward and forward sheets of the first package moiety are joined together, in each case with the interior sides of the rearward and forward sheets of the first package moiety facing one another, so that the first package moiety forms a first partial enclosure; and (b) a second package moiety comprising (i) a first rearward sheet having an exterior side and an interior side, having opposed distal and proximal ends and having opposed first and second side edges, and (ii) a forward sheet having an exterior side and an interior side, having opposed distal and proximal ends and having opposed first and second side edges, wherein the distal ends of the rearward and forward sheets of the second package moiety are joined together, wherein the first side edges of the rearward and forward sheets of the second package moiety are joined together and wherein the second side edges of the rearward and forward sheets of the second package moiety are joined together, in each case with the interior sides of the rearward and forward sheets of the second package moiety facing one another, so that the second package moiety forms a second partial enclosure;

wherein the proximal ends of each sheet include a tip portion and an inward portion;

wherein the proximal end of at least one of the sheets of the first package moiety is folded and disposed with its exterior side in contact with an adhesive layer on the front side of the substrate;

wherein the proximal end of at least one of the sheets of the second package moiety is folded and disposed with its exterior side in contact with an adhesive layer on the front side of the substrate;

wherein the exterior side of the forward sheet is coated with a low adherence material;

wherein the two proximal ends of the rearward sheets of the first and second package moieties are joined together; and wherein the two proximal ends of the forward sheets of the first and second package moieties are joined together;

so that, the first and second package moieties cooperate to provide a joined enclosure with the substrate disposed therein.

20. The combination of claim 19 wherein the low adherence material is a fluorocarbon.

21. A combination of a planar substrate and a package for housing the planar substrate, the substrate having a front side and a back side, the front side comprising a central portion and opposed first and second end portions, at least one end portion having an adhesive coating disposed thereon, the package comprising:

(a) a first package moiety comprising (i) a rearward sheet having an exterior side and an interior side, having opposed distal and proximal ends and having opposed first and second side edges and (ii) a forward sheet having an exterior side and an interior side, having opposed distal and proximal ends and having opposed first and second side edges, wherein the distal ends of the rearward and forward sheets of the first package moiety are joined together, wherein the first side edges of the rearward and forward sheets of the first package moiety are joined together and wherein the second side edges of the rearward and forward sheets of the first package moiety are joined together, in each case with the interior sides of the rearward and forward sheets of the first package moiety facing one another, so that the first package moiety forms a first partial enclosure; and (b) a second package moiety comprising (i) a first rearward sheet having an exterior side and an interior side, having opposed distal and proximal ends and having opposed first and second side edges, and (ii) a forward sheet having an exterior side and an interior side, having opposed distal and proximal ends and having opposed first and second side edges, wherein the distal ends of the rearward and forward sheets of the second package moiety are joined together, wherein the first side edges of the rearward and forward sheets of the second package moiety are joined together and wherein the second side edges of the rearward and forward sheets of the second package moiety are joined together, in each case with the interior sides of the rearward and forward sheets of the second package moiety facing one another, so that the second package moiety forms a second partial enclosure;

wherein the proximal ends of each sheet include a tip portion and an inward portion;

wherein the proximal end of at least one of the sheets of the first package moiety is folded and disposed with its exterior side in contact with an adhesive layer on the front side of the substrate;

wherein the proximal end of at least one of the sheets of the second package moiety is folded and disposed with its exterior side in contact with an adhesive layer on the front side of the substrate;

wherein the tip portions of the proximal ends of at least one of the sheets of each of the first and second package moieties adhere to a greater extent to the adhesive layer than do the non-tip portions of such sheets;

wherein the tip portions of the proximal ends of at least one of the sheets of each of the first and second package moieties are uncoated, and the non-tip portions of such sheets are coated with a low adherence material;

wherein the two proximal ends of the rearward sheets of the first and second package moieties are joined together; and wherein the two proximal ends of the forward sheets of the first and second package moieties are joined together;

so that, the first and second package moieties cooperate to provide a joined enclosure with the substrate disposed therein.

* * * * *